United States Patent [19]
Shaw

[11] Patent Number: 5,267,961
[45] Date of Patent: Dec. 7, 1993

[54] NONREUSABLE SYRINGE WITH SAFETY INDICATOR

[76] Inventor: Thomas J. Shaw, 1510 Hillcrest, Little Elm, Tex. 75068

[21] Appl. No.: 955,842

[22] Filed: Oct. 2, 1992

Related U.S. Application Data

[63] Continuation-in-part of Ser. No. 843,479, Mar. 6, 1992, Pat. No. 5,188,613, which is a continuation-in-part of Ser. No. 679,627, Apr. 3, 1991, Pat. No. 5,120,310.

[51] Int. Cl.⁵ ............................................. A61M 5/00
[52] U.S. Cl. ..................................... 604/110; 604/195
[58] Field of Search ............... 604/195, 110, 187, 198, 604/263, 220

[56] References Cited

U.S. PATENT DOCUMENTS

| | | | |
|---|---|---|---|
| 4,747,831 | 5/1988 | Kulli | 604/110 |
| 4,838,869 | 6/1989 | Allard | 604/195 |
| 4,874,382 | 10/1989 | Lindemann et al. | 604/198 X |
| 4,904,242 | 2/1990 | Kulli | 604/110 |
| 4,932,940 | 6/1990 | Walker et al. | 604/110 |
| 4,955,870 | 9/1990 | Ridderheim et al. | 604/195 |
| 5,007,903 | 4/1991 | Ellard | 604/195 |
| 5,084,029 | 1/1992 | Tagliaferri et al. | 604/195 |
| 5,092,853 | 3/1992 | Couvertier, II | 604/195 |
| 5,114,410 | 5/1992 | Batlle | 604/110 X |
| 5,120,310 | 6/1992 | Shaw | 604/110 |

*Primary Examiner*—John D. Yasko
*Attorney, Agent, or Firm*—Hubbard, Thurman, Tucker & Harris

[57] ABSTRACT

A nonreusable syringe is provided having an automatically retracting hypodermic needle to prevent accidental injury after injection or undesirable reuse of the syringe. The needle is retracted by a spring located behind the syringe piston and disposed to prevent re-extension of the needle after use. A locking mechanism holds the needle in position for injection. The piston includes means to release the locking mechanism as injection is completed to automatically retract the needle into the syringe. The syringe tip seal is not in frictional contact with the needle, eliminating drag on the needle during retraction. A safety indicator is provided to indicate previous use.

20 Claims, 8 Drawing Sheets

FIG. 24

NONREUSABLE SYRINGE WITH SAFETY INDICATOR

CROSS REFERENCE TO RELATED APPLICATION

This is a continuation-in-part of my copending U.S. patent application Ser. No. 07/843,479 filed Mar. 6, 1992, now U.S. Pat. No. 5,188,613 which in turn was a continuation-in-part of my U.S. patent application Ser. No. 07/679,627, entitled Nonreusable Syringe, filed Apr. 3, 1991, now U.S. Pat. No. 5,120,310, for which benefit is claimed under 35 U.S.C. §120.

BACKGROUND OF THE INVENTION

This invention relates to a syringe device and more particularly to a nonreusable syringe having an automatically retracting hypodermic needle to prevent reuse of the syringe.

Many communicable diseases are commonly spread by contacting bodily fluids of an infected person. Reuse of hypodermic syringes is one of the most common ways for such contact, particularly among drug users. Various mechanisms are provided in medical facilities for the disposal or destruction of syringes and hypodermic needles after usage. However, it is not uncommon for a medical worker to be scratched or punctured by a needle after usage and before disposal, resulting in injury and exposure to disease.

Various syringes have been devised for retracting the needle into the syringe or otherwise disarming the syringe after it has been used. U.S. Pat. No. 4,874,382 to Lindemann et al. discloses a safety syringe having a needle which is retracted into a protective sheath inside the syringe. After the needle has been used, it may be withdrawn into the sheath by a coil spring which is actuated by the user depressing a trigger mechanism. However, such a device provides no protection against a user desiring to reuse the syringe who would simply not activate the mechanical trigger.

Another device shown in U.S. Pat. No. 4,838,869 to Allard also provides a protective sheath within the syringe into which the hypodermic needle is withdrawn after usage. In this device, depression of the syringe plunger engages protrusions holding the spring loaded needle so as to release the needle for retraction into the sheath. However, the use of a protective sheath substantially reduces the volume available in the syringe for fluid. Moreover, the strength of the spring is substantially limited by restricting its size to the diameter of the sheath, limiting the effectiveness of overcoming friction of the seal against the needle so as to retract the needle. Furthermore, the use of an inner sheath in a syringe restricts the view of the user in detecting undesirable bubbles in the syringe fluid.

An effective means of indicating that the syringe plunger has been moved is a needed safety feature to assure that a new syringe has never been used.

SUMMARY OF THE INVENTION

The present invention provides a nonreusable syringe apparatus which overcomes these problems in the prior art. The syringe has a retractable hypodermic needle mounted on a thin rod which extends to a large spring located behind the plunger. Thus, strong retraction force is applied without using syringe fluid space. Also, the hypodermic needle is not in substantial contact with the syringe seal so that there is essentially no friction force to be overcome in retracting the needle. In addition, the needle retracts automatically as soon as the syringe has released all of its fluid, eliminating any chance of accidental injury or intentional reuse of the needle once the fluid has been emitted. Moreover, as retraction begins, the needle breaks the vacuum with the skin so that undesired blood and body fluids are not extracted from the patient as the needle is removed.

In one embodiment, the present invention comprises a spring having a retractable needle for injecting fluid into a body which includes a hollow tubular member providing the cavity for the fluid, a plunger disposed partially within the tubular member having piston means in slidable seal contact with the inner walls of the tubular member to form a chamber for the fluid, needle means in the fluid chamber in sealed contact with one end of the tubular member and having a needle extending therethrough to inject the fluid, resilient means disposed entirely behind the piston means and connected to the needle means, being biased to retract the needle into the fluid chamber, lock means connecting the needle means to the tubular member to maintain the seal contact of the needle means to the tubular member, and release means to automatically disengage the lock means and enable retraction of the needle upon actuation of the plunger.

In one variation of this embodiment, the plunger comprises an oppositely spaced apart pair of plunger arms in which the resilient means is positioned around the outside of the arms to allow for a larger and stronger resilient means, if desired.

In a third embodiment, the resilient means is connected to the top of a thin rod means which moves with the needle. The rod means has a biased safety clip which releasably engages the plunger in its depressed position with respect to the tubular body of the syringe. The biased slip covers brightly colored indicia. When the plunger is partially retracted, the clip releases from the plunger and the colored indicia becomes visible through the wall of the syringe to indicate that the plunger has been moved from its shipping position. This serves as a permanent warning that the syringe has been made ready to use, as a further check on possible tampering. Once the clip has been released, it cannot be reengaged and does not interfere with the automatic retraction of the needle assembly which occurs as before when the plunger is fully depressed.

In a fourth embodiment, the plunger assembly may comprise a substantially cylindrical shape forming a hollow cylinder having slots for a spring retaining means fixed to the syringe body to allow the plunger to be moved within the body without interference. The needle assembly may have an arming bar to facilitate seating the needle assembly in the locking means. The arming bar automatically arms the needle assembly for retraction when the plunger is moved.

A fifth embodiment employs a resilient member surrounding the plunger, having one end supported by a stop in the tubular body and an opposite end connected to the upper end portion of a needle rod tensioned to exert a retraction force. A biased arming bar at the end of the needle rod engages a retainer on the plunger when the plunger is depressed. Force exerted on the plunger is transmitted to the needle assembly by the arming bar sufficient to engage a locking means which holds the needle assembly. When the plunger is withdrawn, the arming bar is triggered to spring into a noninterfering neutral position which arms the needle assembly automatically for subsequent retraction by the resilient member. The arming bar serves to simplify assembly, protects against accidental "firing" and itself visibly shows that the plunger has not been moved previously.

A sixth embodiment has the same features as the fifth embodiment except that the stop is positioned down inside the tubular body and the upper end of the needle rod member extends above the spring, one end thereof being connected to the needle assembly to provide retraction force by compression of the spring. A large spring can be used to provide a greater retraction force. Assembly is simplified.

A seventh embodiment has the same essential elements as the previous embodiments in that it has a tubular body, a plunger and piston, a retractable needle assembly, resilient means and a locking means in which the needle rod has surfaces which lock in cooperation with a portion of the syringe body. Like the fifth embodiment, the plunger can be used to engage the locking means which simplifies assembly. The needle assembly and plunger are frictionally engaged and installable as a unit into the syringe body. The syringe may be shipped with the needle in the retracted position.

Locking means are formed by using transverse extensions of the needle rod which may be locked under fingers formed in a widened upper part of a hollow tubular syringe body or under locking tabs formed within the widened upper body. Release means on the plunger disengage and release the locking means by spreading the sides of the upper tubular body to automatically release the fingers from the needle rod extensions as the plunger expels the last fluid to be injected.

A separable portion of the piston engages a groove or expansion on the needle rod in order to use the plunger to move the needle rod into the extended and locked position. Sufficient force applied to the plunger places the transverse extensions of the needle rod just under locking surfaces on the fingers or in the larger diameter tubular body portion. Additional pressure on the plunger then separates the separable portion of the piston away from the piston so that the unseparated portion of the piston and plunger are free to slide independently in sealed contact with the needle rod while the needle assembly remains extended and locked. The separable part of the piston becomes permanently attached to the needle rod to serve as indicia to warn that the syringe has been used. It may be a bright contrasting color for better visibility. Depression of the plunger causes automatic and permanent retraction of the injection needle into the syringe body.

DETAILED DESCRIPTION OF PREFERRED EMBODIMENTS

In the description that follows, like parts will have the same reference numerals insofar as possible. Subscripts will be used to indicate slightly modified versions of similar parts that have reference numerals without subscripts.

Figures 1, 2:
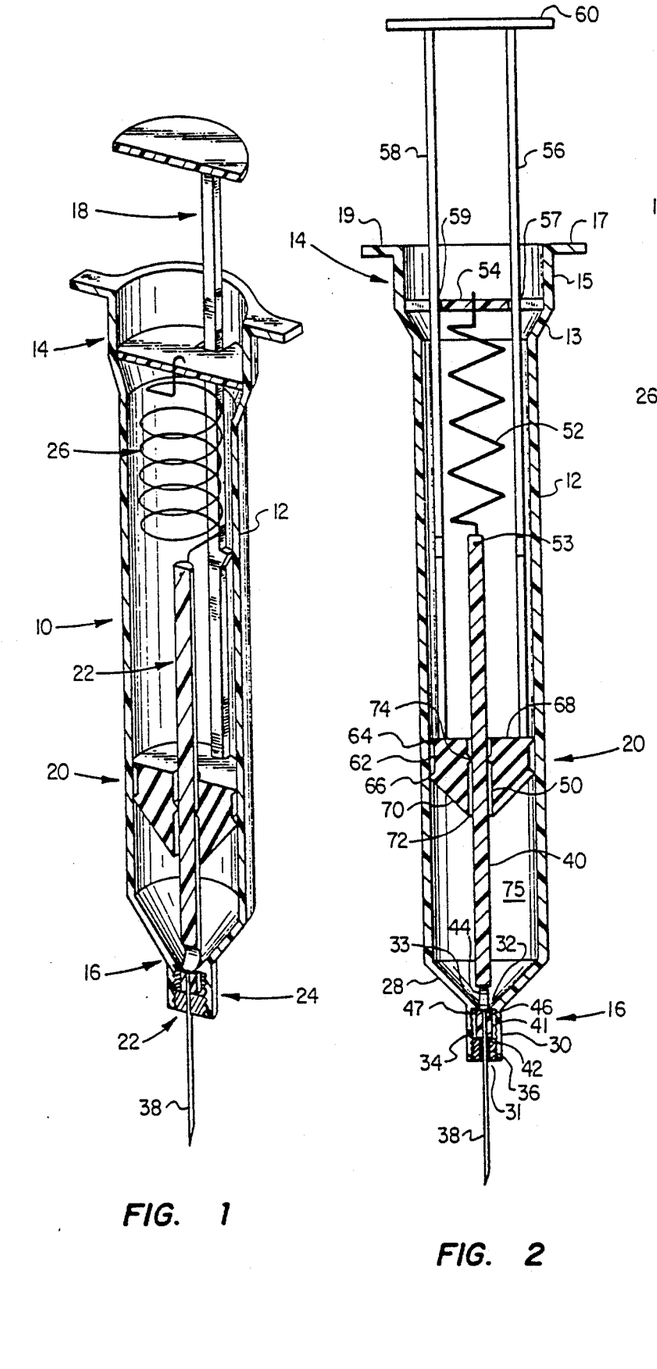
FIG. 1 is a perspective cross-section view of a syringe comprising a preferred embodiment of the present invention.
FIG. 2 is an elevational cross-section view of the syringe of FIG. 1 showing the syringe in armed condition with the needle extended.

With reference to FIG. 1, a hypodermic syringe 10 is shown comprising a cylindrical tube 12 having an open end 14 and a closed end 16. A plunger assembly 18 extends out of the open end of the syringe tube and is connected to a piston assembly 20 which is slidably movable along the inner walls of tube 12. A needle assembly 22 includes a needle 38 extending through closed end 16 of tube 12. A lock assembly 24 holds the needle assembly in position with needle 38 extended. Needle assembly 22 is connected to a resilient spring assembly 26 which is biased to retract needle assembly 22 into tube 12.

Syringe 10 is constructed to retract needle 22 into tube 12 automatically during the course of use of the syringe as the last step of injecting fluid into a patient. The needle retraction prevents any possibility of infection of a health care worker by accidental contact with the needle after injection. The automatic needle retraction also prevents any further use of the needle for further injections.

Locking now at FIG. 2, tube 12 is preferably a cylinder having a unitary radius throughout except at open end 14 and closed end 16. The radius of tube 12 increases near open end 14 to form an annular ridge 13. Tube 12 extends further at the increased radius to form wall 15 terminating in radially extending fingers 17 and 19.

Closed end 16 of tube 12 is formed by a cone-shaped section 28 in which the radius of tube 12 tapers to form a restricted tube 30 having a small axially centered tubular opening 31. At the point where cone-shaped section 28 joins restricted tube 30, lock tabs 32 and 33 extend radially inward to form a locking mechanism to be discussed later. The interior wall of restricted tube 30 has threads 34 and a threaded tubular tip seal 36 positioned to seal off tubular opening 31.

Figures 5, 6:
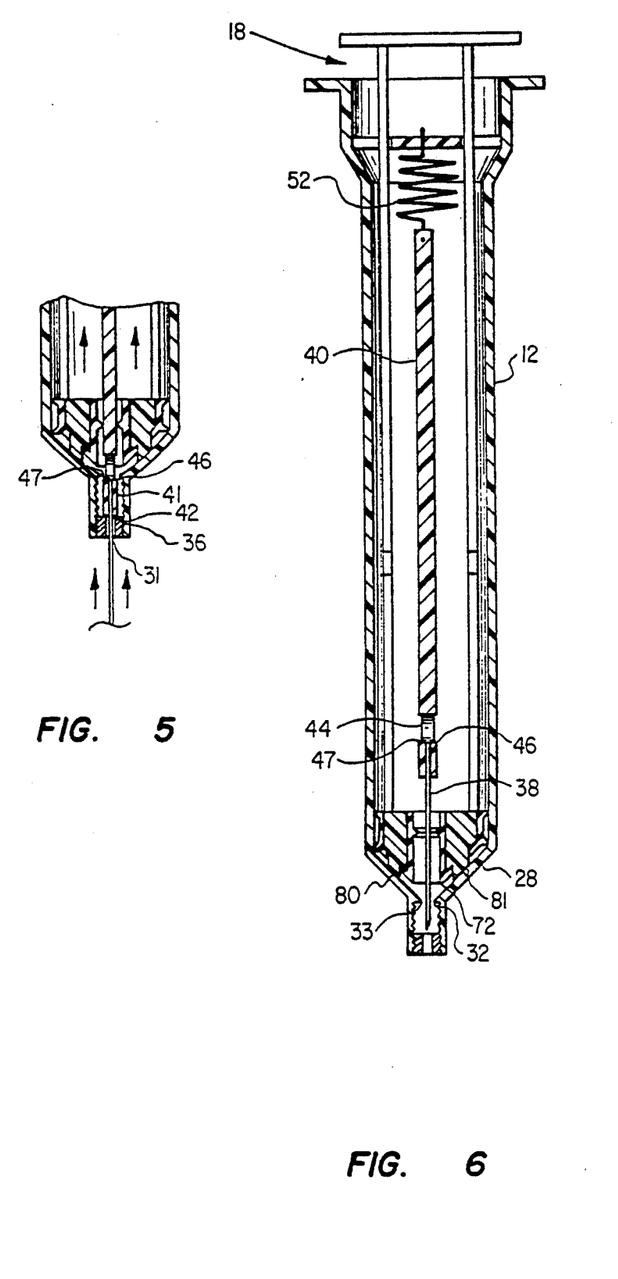
FIG. 5 is an exploded detailed view in cross-section of the lower portion of the syringe shown in FIG. 4.
FIG. 6 is an elevational cross-section view of the syringe shown in FIG. 3 in unarmed state with the needle retracted into the syringe cylinder.

A hollow sharpened needle 38 extends through restricted tube 30 and tip seal 36. The other end of needle 38 is inset into a rod 40 which extends downward through piston assembly 20 and into tubular opening 31 of tube casing 12. As best seen in FIG. 5, rod 40 has a rod end 41 forming a shoulder 42 which abuts at the end of tip seal 36 thereby sealing off tubular opening 31. Thus needle 38 is not in contact with seal 36, eliminating any frictional pull on needle 38 as it retracts. Needle 38 is inset in rod end 41 and extends to a transverse hole 44 in rod 40 which communicates with the hole in hollow needle 38. At the junction of transverse hole 44 and rod end 41, shoulders 46 and 47 abut against lock tabs 32 and 33, which holds needle 38 in its extended position as shown.

Rod 40 extends axially through a channel 50 in piston 20. A spring 52 is connected through a hole 53 in the end of rod 40 and extends axially to connect to a spring support member 54 resting radially on the slanted annular ridge 13 of tube 12. Preferably, support member 54 is permanently affixed to the walls of tube 12 to prevent removal of needle assembly 22 after use.

Plunger assembly 18 consists of two plunger arms 56 and 58 extending through apertures 57 and 59 in spring support 54 and terminating at piston assembly 20. Plunger bars are connected at their upper end to a flat disk 60 for depressing the plunger during use. Upon depression of plunger 18, annular tip 72 impacts lock tabs 32 and 33 directly and flexes them away from shoulders 46 and 47 of rod end 41, thereby enabling retraction of needle 38.

Piston assembly 20 is comprised of a circular piston 62 slidable along the inner walls of tube 12 and having upper and lower annular seals 64 and 66 in slidable contact with the inner walls of tube 12 and forming a fluid seal therewith. Piston 62 has a flat upper surface 68 to which plunger arms 56 and 58 are attached. A conical lower surface 70 slants inward from annular seal 66, ending in an annular tip 72 which forms the lower end of tubular channel 50. Piston 62 also has an annularly extending seal 74 extending within tubular channel 50 to form a fluid seal with rod 40. Thus, a fluid chamber 75 is formed by conical surface 70, annular seal 74, and outer seals 64 and 66 at the upper end. The rest of the fluid chamber 75 is formed by the walls of tube 12 which taper downward in cone-shaped section 28 to restricted tube 30 which is sealed off by tip seal 36 and rod end 41.

Figure 3:
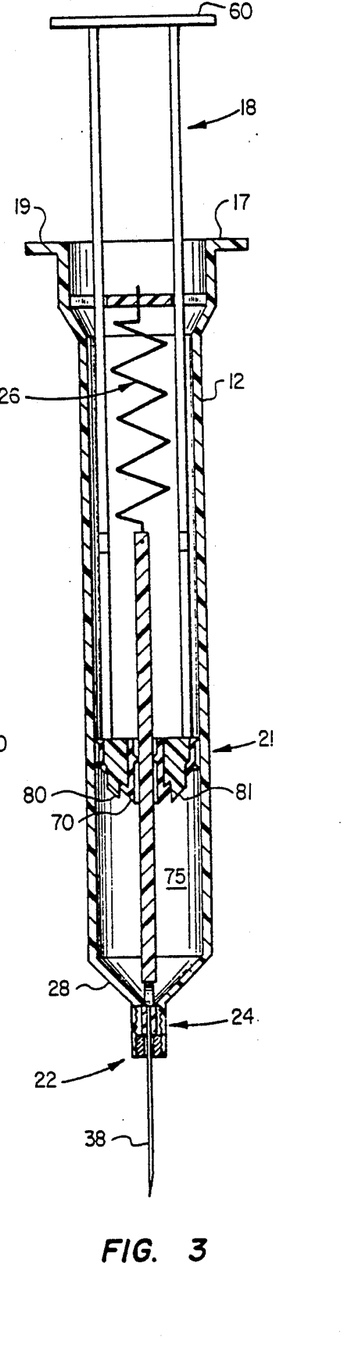
FIG. 3 is an elevational cross-section view of another embodiment of the present invention showing the syringe in armed state with the needle extended.

An alternate embodiment is shown in FIG. 3 having the same structure as the syringe of FIGS. 1 and 2 except with regard to piston assembly 21. In this embodiment, piston assembly 21 is identical to piston assembly 20, except that it includes dual cusp abutments 80 and 81 protruding downward from conical surface 70 to make contact with cone-shaped section 28 of the syringe tube, 12 when the plunger assembly 18 is fully depressed.

Spring support 54 preferably also includes a shipping safety stop (not shown) comprising a rectangular-shaped member resting on top of spring support member 54 so as to impact the lower surface of plunger disk 60. The shipping safety stop is of sufficient height to prevent the plunger assembly 18 from being depressed to the point where piston assembly 20 impacts locking assembly 24 releasing needle assembly 22 to be withdrawn into the tube. The safety stop may also include a spring biased to automatically fold the stop onto spring support 54 once the plunger assembly 18 has been retracted so as to allow a full stroke of the plunger 18 during injection.

Regarding materials, preferably the spring 52 is steel, needle 38 is corrosive-resistant steel, plunger 62 is a medium-soft rubber, tip seal 36 is medium-hard rubber and all other materials are plastic.

The operation of syringe 10 will now be described. As shown in FIG. 3, the plunger assembly 18 is retracted to draw fluid into chamber 75 through hollow needle 38. After fluid is drawn into chamber 75, it may be injected by inserting needle 38 into the body of a patient and by grasping fingers 17 and 19 while pressing on plunger disk 60, thus moving the plunger assembly 18 into the syringe casing 12. During depression of the plunger assembly 18, fluid is forced out of chamber 75 through needle 38 into the patient.

Figure 4:
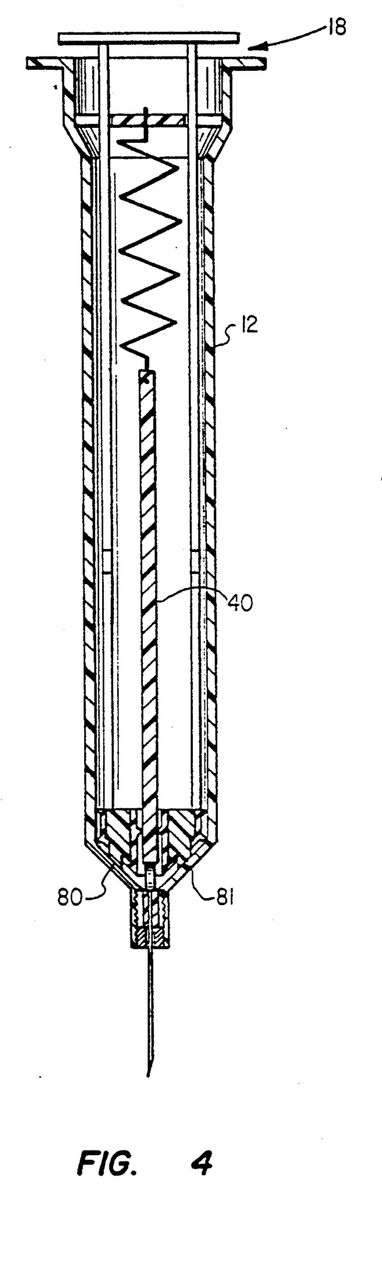
FIG. 4 is an elevational cross-section view of the syringe in FIG. 3 with the plunger fully depressed.

With reference now to FIGS. 4, 5 and 6, when plunger assembly 18 is fully depressed, the dual cusp abutments 80 and 81 impact the cone-shaped section 28 of tube 12. Preferably section 28 is thin-walled and designed to flex ovally when pushed by dual cusp abutments 80 and 81 so as to flex the lock tabs 32 and 33 holding the needle assembly 24 in place. Lock tabs 32 and 33 then release shoulders 46 and 47 of rod end 41, as best seen in FIG. 5. The resulting action enables spring 52 to fully retract rod 40, thereby retracting needle 38 completely within syringe tube 12, as shown in FIG. 6.

Figure 7:
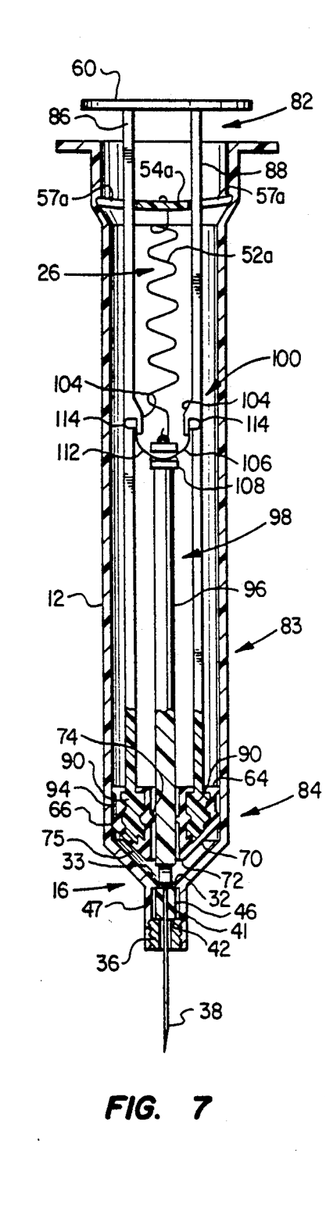
FIG. 7 is an elevational cross-section view of the third embodiment. A biased clip mechanism engages the plunger in its depressed position with indicia covered by portions of the clip.
Figure 8:
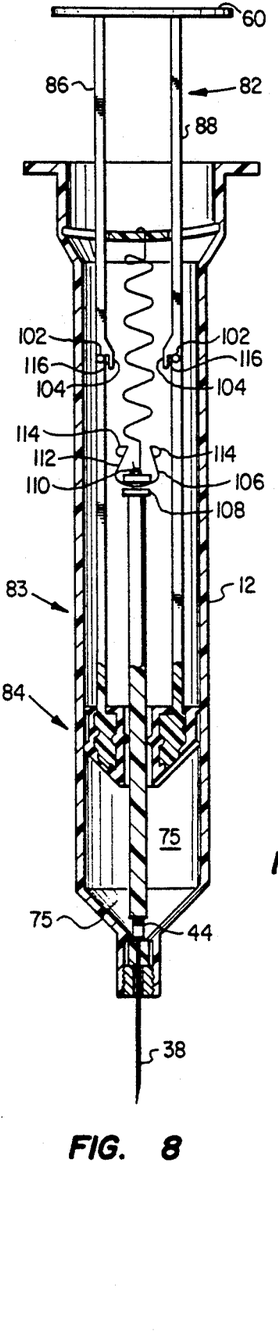
FIG. 8 shows the embodiment of FIG. 7 with the plunger partially retracted to release the clip to its unbiased position, revealing warning indicia on the plunger.

In FIGS. 7 and 8, a third embodiment of the invention is illustrated. A hypodermic syringe 83 has a hollow tubular body 12, a plunger assembly 82 with safety indicator, piston assembly 84 and needle assembly 98. Safety indicator plunger assembly 82 is connected to piston assembly 84, which is quite similar to piston assemblies 20 and 21. Plunger assembly 82 has plunger arms 86,88 which are connected by a disk 60. The lower extremity of arms 86,88 has an annular portion 90 which serves as a support for rubber piston 94 which has the same attributes as piston 62 of piston assembly 20. Consequently, the same reference numerals will be used to denote like portions of piston assembly 84. It has a conical lower surface 70, annular tip 72, annular seals 64 and 66, and an internal annular seal 74 to seal elongated rod member 96 of needle assembly 98. The lower end of the rod member 96 is connected to needle 38 and in all respects is the same as shown in FIG. 2. A resilient spring assembly 26 includes a resilient spring member 52. Spring 52 is connected to a spring support member 54a to indicate that it is slightly modified from support member 54 to take into account the slightly closer spacing of arms 86,88 which necessitates deeper apertures 57a in which the plunger arms ride.

Figure 9:
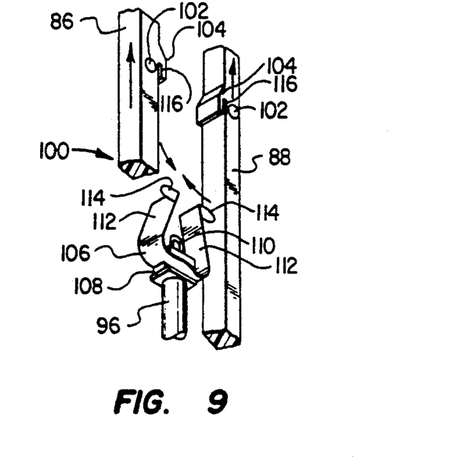
FIG. 9 is a detail perspective view of the clip and portions of the plunger rods and indicia just after the clip has been separated and released from the plunger.
Figure 10A:
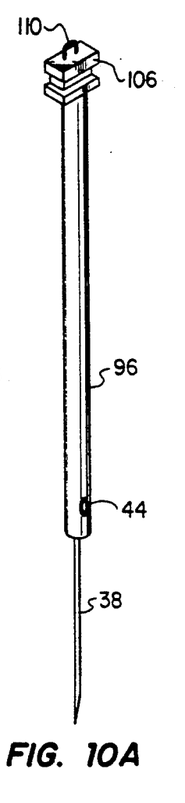
FIG. 10A is a perspective view of a portion of the needle assembly with a clip retainer mounted on the rod which holds the needle.
Figure 10B:
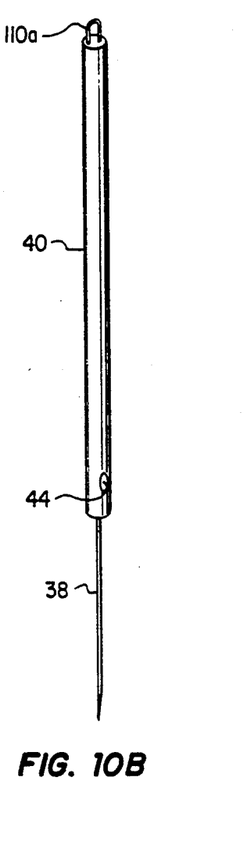
FIG. 10B is a perspective view of the needle and rod with a fastening loop on one end.

FIGS. 7 and 8 show the operation of a safety assembly 100 comprising brightly covered warning indicia 102 and retainers 104 on plunger arms 86,88 (FIG. 9) and a biasable member 106 mounted on holder 108 fixed to the upper end of the elongated rod member 96. FIG. 10A best shows the holder 108 having connector 110 for attaching resilient member 52a. FIG. 10B shows a connector 110a on a rod 40 as an anchor for a resilient spring.

Returning to FIG. 9, biasable member 106, holder 108 and connector 110 are an extension of the needle assembly 98. Biasable member 106 may be a spring clip having a pair of cooperating arms 112 or eared extensions, having ears 114.

In operation arms 112 are biased to releasably engage cooperating slots 116 of retainers 104 in FIGS. 7 and 8. Ears 114 are adapted to cover indicia 102. When plunger 82 is pushed down, biasable spring member 106 is strong enough to transfer the downward force to needle assembly 98 and seat it in locked operative position with tip 41 in contact with seal 36 and the lock means of the tubular body 12 engaged with the lower end portion of rod member 96. This is the way the syringe is furnished for use.

When plunger 82 is withdrawn in FIG. 8 to fill chamber 75 with injection fluid, member 106 being connected to locked rod 96 resists movement and cooperating arms 112 are pulled from retainers 104 and slots 116. This allows biased arms 112 of member 106 to irreversibly close toward the center which arms the needle assembly for subsequent retraction when it is released from the lock means. The warning indicia are visible through the clear wall of the syringe to indicate that the syringe has been used.

When the plunger is depressed to inject the fluid, there is clearance between the now unbiased member 106 and retainers 104. Plunger 82 can move down until piston assembly 84 releases the lock means and the needle assembly is free to move upward into tubular body 12 under influence of resilient spring 52a. The needle is completely retracted into the body and cannot be re-used. The warning indicia remain uncovered.

Figures 11, 12, 13:
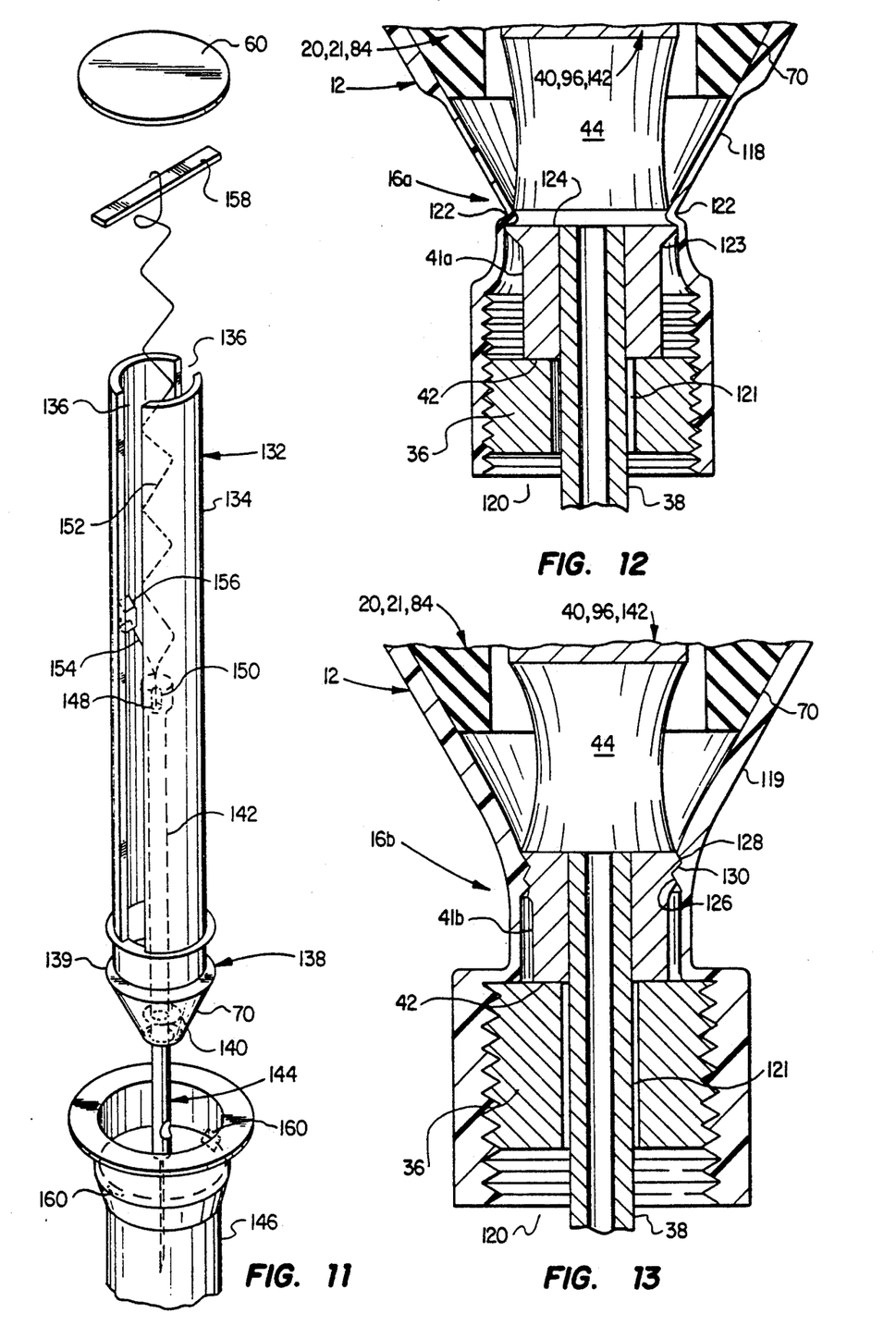
FIG. 11 shows an exploded perspective view of a fourth embodiment having a plunger assembly formed as a hollow cylinder having slots accepting of a spring retaining bar and equipped with a spring loaded arming bar.
FIG. 12 shows a partial elevational cross-section of any of the embodiments showing a modified form of a release means holding a needle assembly in armed state.
FIG. 13 shows a partial elevational cross-section of any of the embodiments showing another modified form of a release means and needle assembly in armed state.

In FIGS. 12 and 13, hollow tubular body 12 may have a modified closed end 16a or 16b. Body 12 has a lower end 16a, 16b, having a tapered conical shaped wall 118,119. The tip 41 of the elongated rod may be slightly modified to tip 41a, 41b as shown.

In FIG. 12 the lower end 16a has a tubular axially-centered opening 120 threaded to hold tip seal 36 therein. Annular locking means 122 located above opening 120 comprises an annular ring formed in wall 118 for engaging an annular locking surface 124 on the rod tip or lower end 41a which terminates in sealing surface 42. Locking surface 124 is spaced above sealing surface 42 to simultaneously lock the tip and seal against seal 36. Annular locking means 122 is formed around the most restrictive portion of tapered walls of body 12. Lower end 41a of rod member 40,96,142 is preferably relieved starting at 123 to reduce frictional resistance during retraction. Gap 121 separates seal 36 from needle 38 to eliminate friction there. When the plunger of choice is depressed, wall 70 of pistons 20,84,138 or annular protrusions on piston 21 flex or spread wall 118 to unlock and release the seated needle assembly which is then retracted. Wall 70 may have a slightly different taper from wall 118 to facilitate release. It is desirable to minimize empty space above seal 36 around tip 41a below the lock means to reduce air entrainment.

In FIG. 13, modified lower end 16b has tubular axially centered opening 120 threaded to receive seal 36. At the most restricted portion of conical tapered wall 119 are several internal threads 126 comprising annular locking means 128. Cooperating threads 130 are formed on modified rod end 41b which like modified end 41a may be used with any of the elongated needle rods disclosed herein. Cooperating threads 130 comprise a locking surface on the lower end of an elongated rod member 40,96,142. The needle rod member may be screwed into position with surface 42 against seal 36. Downward force on the needle rod may also engage locking means 128 by flexing of wall 119 to slip the threads 126,130 relative to each other and seat needle rod tip member shoulder 42 in sealed contact with seal 36 with needle 38 held extended in operative position.

Downward force on the piston when the plunger is depressed causes surface 70 (or a protrusion thereon) to come into contact with and slightly flex and expand wall 119 to release the cooperating threads 126,130 of locking means 128 so that the needle rod is free to respond to retraction force supplied by a resilient means as has been described.

FIG. 11 represents a fourth embodiment having a plunger assembly 132 formed as a hollow cylinder 134 having opposed longitudinal slots 136. Piston assembly 138 is located at the lower end of plunger 132. The piston may be molded integral with or fixed to plunger 132 or plunger 132 may have a piston 20 or 21. Piston assembly 138 has a conical surface 70 for releasing a locking means. Piston assembly includes a groove 139 for an "O" ring type seal against the inner walls of syringe body 146. Piston 138 also has a sliding seal 140 to seal rod 142 of needle assembly 144. This seal may be an "O" ring seal. Plunger assembly 132 fits into syringe body 146 which may have a locking and release mechanism for the needle assembly like FIGS. 1–6, 7, 12 or 13.

The upper end of elongated rod 142 has transverse opening 148 intersecting upright groove 150 extending to the distal upper end of the rod. Opening 148 and groove 150 secure one end of spring 152. Connected to the upper end portion of rod 142 is an arming bar 154 which is releasably engaged with retainer 156 on the wall of cylinder 134. Operation of the arming bar will be discussed further in connection with FIGS. 14–16. The opposite end of spring 152 is supported by bar 158 which is fixed in notches 160 at the top of tubular body 146 and serves as a guide to orient the plunger, if desired, while it is moved. The slotted openings 136 permit the plunger to be withdrawn without interference from bar 158. Thumb disc 160 is secured to the upper end of the plunger. Release of the arming bar occurs as soon as the plunger is moved upward from its fully depressed position with the needle assembly locked. It operates like FIGS. 14–17.

Figure 14:
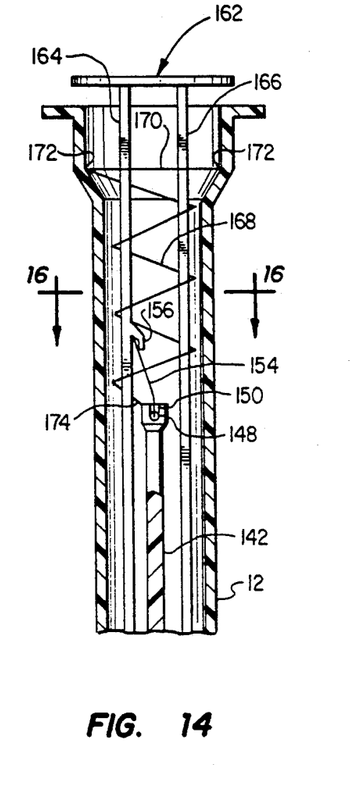
FIG. 14 is a partial elevational cross-section of a fifth embodiment showing an alternate arrangement of the plunger and resilient means and a spring loaded arm which serves as an arming bar shown in unarmed state.
Figures 15, 17:
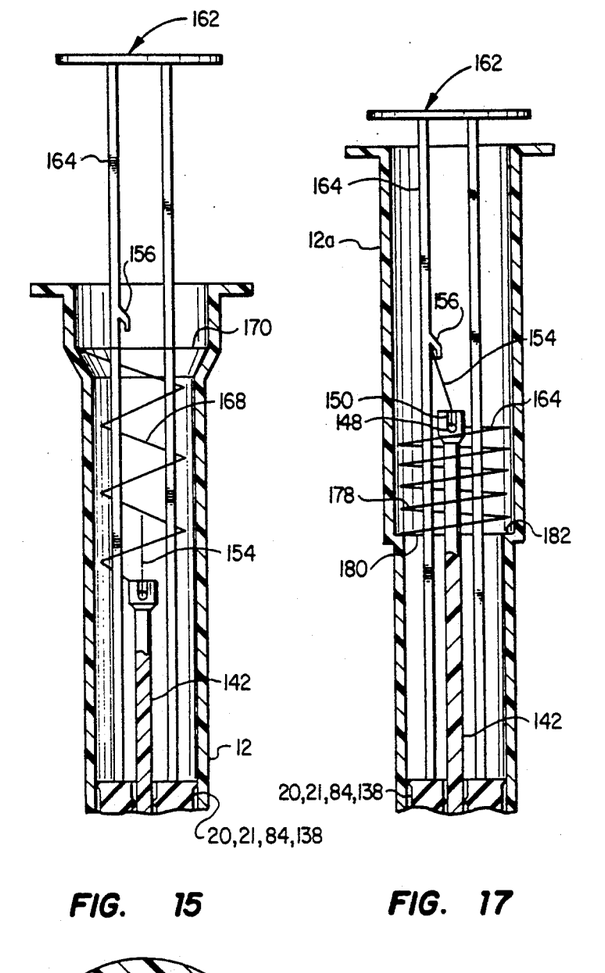
FIG. 15 is a partial elevational cross-section of the syringe of FIG. 14 showing the armed state which permanently results when the plunger is partially withdrawn from the hollow body to disengage the spring loaded arm.
FIG. 17 is a partial elevational cross-sectional view of a sixth embodiment showing another alternate arrangement of the plunger and resilient means including a spring loaded arming bar in initial unarmed position.
Figure 16:
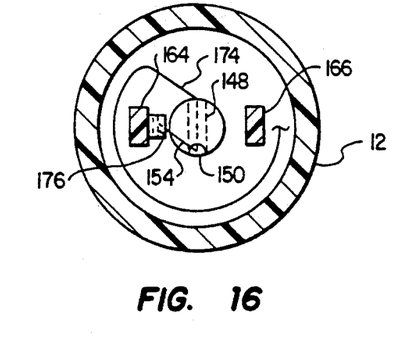
FIG. 16 shows a cross section on line 16—16 of FIG. 14 with an end of the spring loaded arm in a retainer on the plunger.

FIGS. 14–16 illustrate the idea of the arming bar in a fifth embodiment, it being understood that the bottom half of the syringe is like any of the FIGS. previously discussed. Rod 142 extends upwardly in sliding sealed contact through a piston assembly 20, 21, 84 or 138, which in this case would be connected to and operated by slightly modified plunger assembly 162 having a pair of arms 164,166. Rod 142 extends downwardly below the piston as part of a needle assembly which is releasably locked and unlocked by the piston as has been previously described in connection with the other FIGS. FIG. 14 shows the position with the plunger and piston fully depressed and the needle assembly locked as in FIG. 7.

Spring 168 is a resilient member which circumscribes and surrounds plunger arms 164,166, having an enlarged upper end 170 secured in an annular stop 172 formed at a flared open end of hollow tubular body 12 and preferably sealed in place by adhesive or mechanical means so that the piston cannot be removed.

The opposite lower end 174 of spring 168 is connected to the upper end portion of elongated rod member 142 via transverse opening 148 and interconnected upright groove 150. Spring loaded arming bar 154, which conveniently comprises an extension of spring wire 158, extends upwardly through groove 150 to releasably engage a retainer 156 formed on plunger arm 164. Spring 168 is biased to exert retraction force on elongated rod 142. During assembly the arming bar maintains the positional relationship between the plunger assembly and rod member as shown in FIG. 14.

Arming bar 154 may include bent end portion 176, best seen in FIG. 16, to engage a slot in retainer 156.

Arming bar 154 is sturdy enough to engage the locking means and locking surface on tubular body 12, and a rod member 40,96,142, when downward force is applied to the rod member via the arming bar when the plunger is depressed. This is the preferred position of the syringe for shipment before use.

FIG. 15 illustrates what happens when the needle assembly 162 is armed by moving plunger 162 upward from the pre-use position in order to draw fluid into the syringe for injection. Rod 142 remains locked with the needle assembly in operational position with needle 38 extended. Retainer member 156 moves upward and arming member 154 is released and triggered to its neutral unbiased position axially centered in body 12. Spring member 168 is now poised to retract the needle assembly immediately when the needle assembly is subsequently unlocked in response to full downward movement of the plunger. The arming member is permanently and irreversibly out of the way once it is armed in this manner.

It should be noted that the arming bar makes assembly simple by seating the needle assembly to locked position when the plunger is depressed. It prevents accidental retraction of the needle if someone should apply force to the plunger before the plunger is withdrawn for filling. It serves as a visible signal that the syringe has never been used.

FIG. 17 represents a sixth embodiment of the resilient spring, plunger and body arrangement that allows for a resilient spring which provides retraction force to a needle assembly by compression in the spring member. Spring 178 has a lower end 180 resting on annular ledge 182 formed in modified hollow tubular body 12a. Upper end 184 of spring 178 is connected via transverse opening 148 and upright in the upper end of elongated rod member 142 as previously described. The distal upper end portion of spring 178 may conveniently extend upward to serve as spring loaded arming bar 154 which is biased to releasably engage retainer 156 on plunger arm 164 of plunger assembly 162. The operation is as described with respect to FIGS. 14–16. In this case, stop 182 is positioned below the upper end of the elongated rod member so that the spring can operate by compression to retract the needle assembly.

Figure 18:
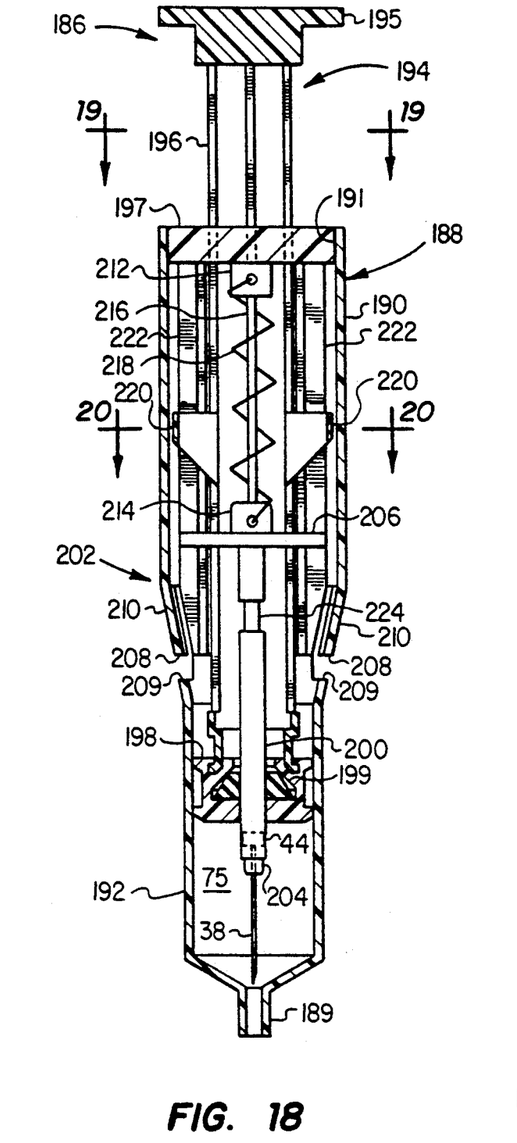
FIG. 18 is an elevational cross-sectional view of the seventh embodiment showing another alternate arrangement of the plunger, needle rod and locking means in an unlocked, unarmed shipping position.
Figure 19:
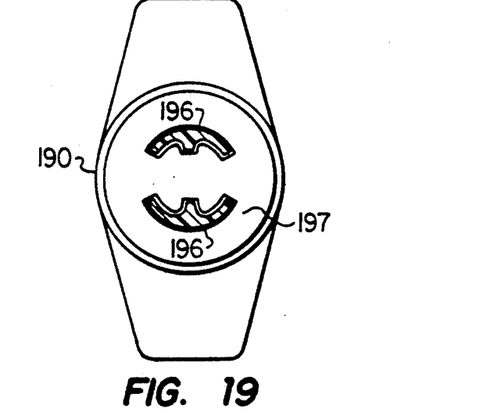
FIG. 19 is a cross-section of the plunger and a plunger guide plug fitted into the open end of the tubular body on lines 19—19 of FIG. 18.

FIG. 18 illustrates the idea of an arming bar which is in the form of a transverse bar 206 on the head of the needle rod which is part of locking means 202 in cooperation with locking surfaces formed in the wall of the syringe body. A locking means 202 is formed in a medial portion of syringe 186. Syringe 186 has a hollow syringe body 188 having plunger opening 191 at an upper end thereof. Hollow syringe body 188 has an enlarged upper portion 190 and a lower portion 192 which terminates in tip 189. The inner walls of lower portion 192 define a variable fluid chamber 75 below a piston means 198 which moves in sliding sealed contact with the walls of the syringe body below a locking means 202 to define the variable fluid chamber.

Plunger assembly 194 has a plunger disk 195 connected to a spaced apart pair of plunger arms 196 which are securely connected to a portion of piston 198. Piston 198 includes annular separable member 199 having tapered edges which fit in a corresponding cavity having tapered walls in the piston.

A movable needle assembly is centrally located in syringe body 188. The needle assembly includes a needle 38 in fluid communication with the end of an elongated needle rod 200 having opening 44 in the lower end thereof. The lower distal end of needle rod 200 includes a seal 204 around needle 38 which can engage and seal the opening in tip 189. Seal 204 may comprise a resilient band fitted over a reduced diameter distal lower end of the needle rod. The needle assembly has a retracted position entirely within syringe body 188 in FIG. 18 and an extended position shown in FIG. 22 wherein needle 38 is sealingly extended from the tip of the body for use. Needle 38 communicates with variable chamber 75 through opening 44 when the needle is in the extended position.

Figure 22:
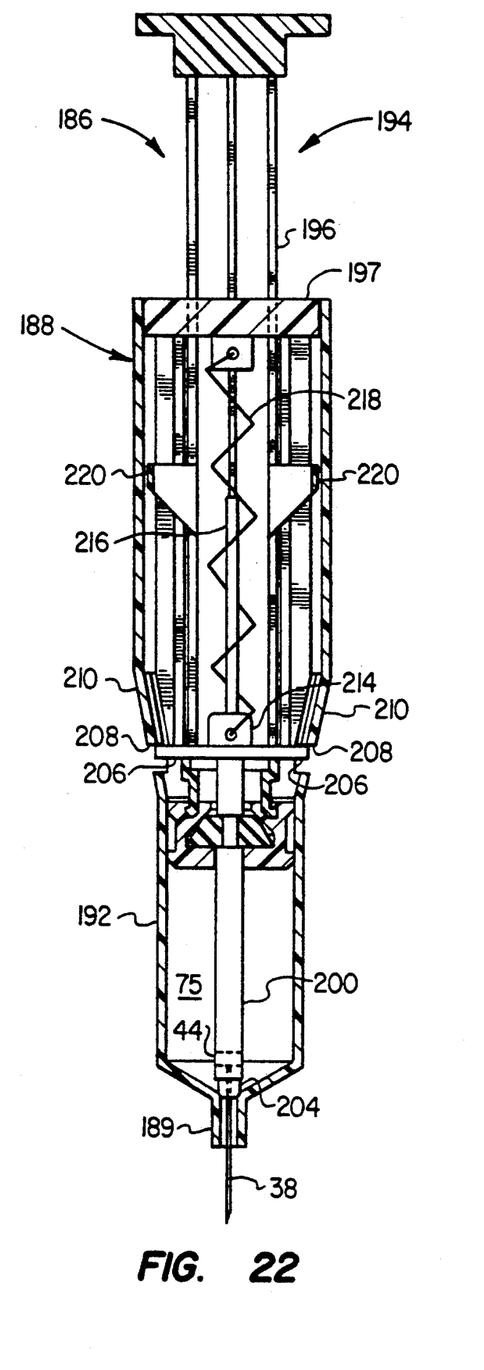
FIG. 22 shows the embodiment of FIG. 21 wherein the plunger has been depressed to lock the needle rod under flexible fingers in the side wall of the syringe body with the separable portion still connected to the piston.
Figure 23:
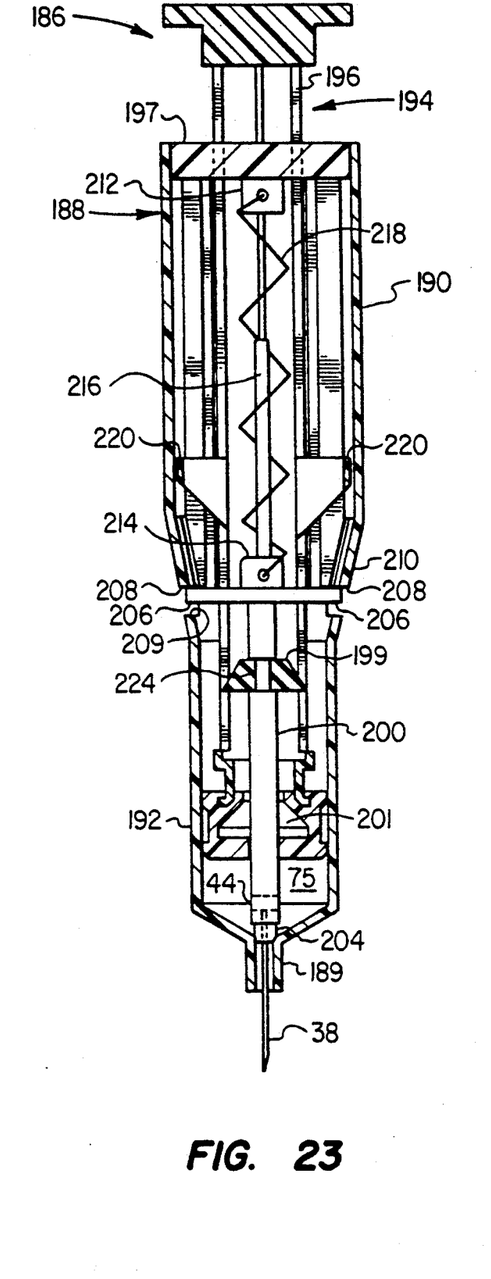
FIG. 23 is the embodiment of FIG. 22 with the separable portion of the piston having been separated from the piston by further depression of the plunger after the needle assembly has been locked into position.

Locking means 202 releasably locks the needle assembly with the needle in the extended position. The upper end portion of needle rod 200 has opposed transverse extensions 206. These comprise one or more locking surfaces moveable with the needle rod to engage one or more cooperating locking surfaces such as locking surfaces 208,209 on syringe body 188. These cooperating surfaces are formed in the syringe body just below the enlarged portion 190. Lowermost cooperating locking surfaces 209 may be provided. They are adapted to contact the lower surfaces of transverse extensions 206 so as to establish an absolute lowermost limit of travel of the needle assembly. Normally, they will not come into contact because resilient seal 204 engages the opening in tip 189 which arrests further movement of the rod once the tip is sealed. The upper surfaces of transverse extension 206 are adapted to engage cooperating locking surfaces 208 on opposed fingers 210 formed in the lowermost portion of enlarged upper syringe body 190 as best indicated in FIGS. 22 and 23. The locked position is established by means of the plunger assembly in a manner to be described subsequently.

Figure 27:
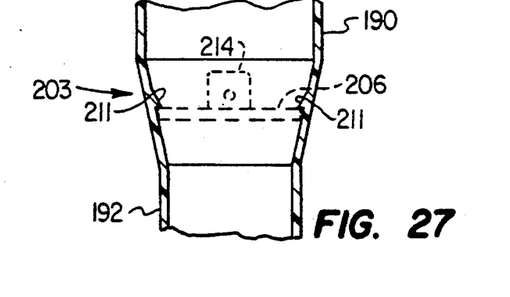
FIG. 27 shows an alternate locking means formed inside the tapered medial portion of the syringe body.

An alternate form of locking means is shown in FIG. 27. In FIG. 27, the medial tapered portion of the syringe body is schematically shown as locking means 203 in which locking tabs 211 are formed on the inside surface of the syringe body wall at a position which will just capture the upper outermost surfaces at the ends of transverse extensions 206. Locking tabs 211 may be short arcs long enough to support the ends of member 206 when it is forced beneath them by slightly expanding the wall of the syringe. A release means is provided by the action of release arms 220 to be described.

A retraction means causes the needle to permanently be withdrawn into the retracted position automatically in response to depression of the plunger to inject fluid. Boss 212 is fixed to the lower surface of plunger guide plug 197 and a corresponding boss 214 is fixed to the upper end of the needle rod with biasing member 218 interconnected therebetween. Biasing member 218 surrounds a stop rod 216 which may be connected at one end to either of bosses 212,214. In either case, biasing member 218 produces a retraction force which draws the needle rod against the stop member when it is unlocked or released from the locking means. This produces a fixed retraction position with the needle 38 entirely withdrawn into the syringe body. The biasing member may be a coil spring which is strong enough to overcome any sliding friction as the needle rod is drawn upward relative to the piston. The biasing member 218 could also be an elastomeric material.

Figure 20:
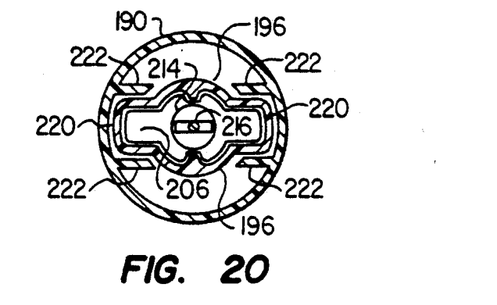
FIG. 20 is a cross-section of a release means on the plunger which includes plunger guides on the tubular wall of the body. The release structure on the plunger surrounds T-shaped extensions extending from the head of the needle rod which engage locking surfaces in an upper enlarged portion of the tubular body to lock the needle assembly into an extended position with the needle extended.

The retraction means includes hollow release arms 220 on the plunger which extend oppositely and are located across the middle of the plunger assembly as best seen in FIGS. 18 and 20. Release arms 220 generally have a U-shape when viewed from above and are extended as continuations of portions of the walls of opposed plunger arms 196 which join to form a hollow opening adapted to receive the transverse ends 206 at the end of the needle rod and allow the end of the needle rod to pass through. Release arms 220 may slide between opposite sets of elongated guide members 222 formed on the inside wall of upper portion 190 of syringe body 188, when the plunger is moved. Release arms 220 and the connecting portions of plunger arms 196 constitute a release on the plunger which unlock or release locking means 202 or 203. Plunger release 220 and transverse extensions 206 of the needle rod are adapted for mutual relief so that the transverse extensions 206 may pass unimpeded through the release portion 220 of the plunger during retraction.

Figure 24:
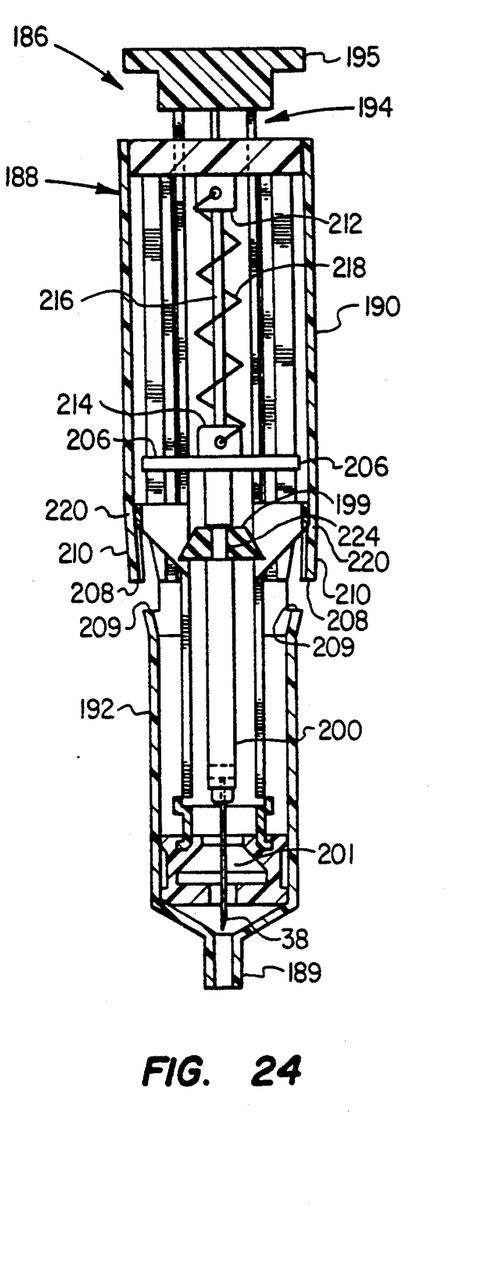
FIG. 24 shows the retracted position of the embodiment shown in FIG. 18-23 with the needle fully withdrawn into the syringe body as a result of full depression of the plunger.

When the plunger is depressed, the release arms 220 move downward until they engage and expand fingers 210 in the side wall of syringe body 190 as seen in FIG. 24. The expansion of the fingers releases cooperating locking surfaces 208 from the locking surfaces on the top of transverse extensions 206. This releases and frees the needle rod which can then pass upward unimpeded through the release portion 220 of the plunger under the influence of biasing member 218. Then and only then is the needle retracted once the needle rod has been locked. In the alternate of FIG. 27, release arms 220 engage the tapered medial wall between syringe portions 190,192 just above locking tabs 211 when the plunger is depressed. Pressure of arms 220 slightly bends the wall outwardly in a slight oval shape enough to spread the locking tabs away from their hold on member 206 which then is free to move upward through the hollow release arms in response to the force of the biasing member to retract the needle.

In operation, the unit can be shipped to the user in the position shown in FIG. 18. Separable member 199 and piston 198 sealingly surround needle rod 200 to such an extent that the rod will move with the plunger unless restrained whereupon it will slide relative to the piston assembly. In the position of FIG. 18, moving the plunger up and down may cause the needle rod to move some. But any frictional engagement between the needle rod and piston is not sufficient to lock the needle rod with the needle in the extended position because spring member 218 would keep the needle rod from moving enough to lock. The plunger engages the needle rod for movement to the locked position by means of a separable member 199 frictionally held within the piston, which falls into groove 224 or passes over and locks onto an expansion on the needle rod when the plunger is moved upward in FIG. 21. The idea here is that there is some connecting means on the needle rod that causes the separable member to lock onto the needle rod with sufficient gripping force to permit the plunger to move the needle rod into the locked position.

Figure 21:
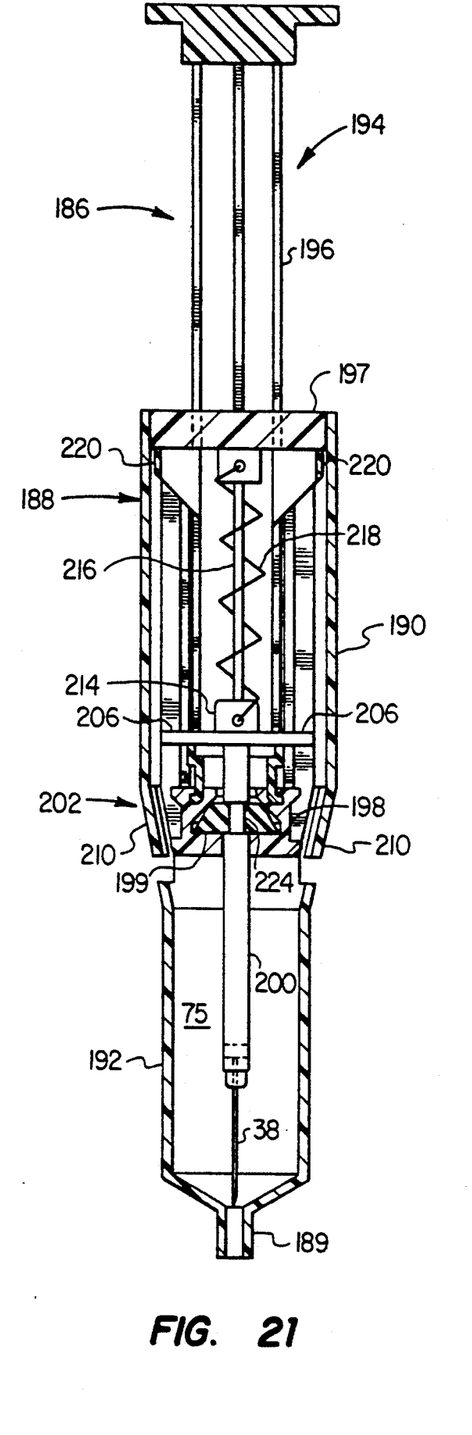
FIG. 21 shows the embodiment of FIG. 18 having a separable portion of the piston engaged in a groove in the needle rod, the plunger being withdrawn in preparation for locking the needle rod with the needle extended.

Separable member 199 is shaped like a donut with tapered wall surfaces. Its wall is severed at one point so it can operate like a split ring. The internal diameter of separable member 199 is smaller than the diameter of the needle rod such that it is expanded leaving a gap where the severed wall exists. When the plunger is retracted from syringe body 188, the needle rod moves upwardly until boss 214 strikes the end of rod 216 which stops any further movement of the needle rod assembly. Continued withdrawal of the plunger causes the piston to slide along the needle rod until the separable member falls into annular groove 224 as shown in FIG. 21. Now the needle rod is temporarily locked to the plunger through its connection with the separable member in the piston. The plunger is at its furthermost extension in FIG. 21. In FIG. 22 the plunger has been pushed back into the syringe body causing locking of the cooperating locking surfaces 208 on transverse extensions 206. The tip is simultaneously sealed by compression of seal 204 with the opening of tip 189.

In another arrangement, the needle rod may have an enlarged diameter annular portion where groove 224 is located that may engage a relieved portion of the separable member or a combination of grooves and enlarged portions whereby a separable member 199 may become attached to the rod member 200 so that the plunger can be used to move and lock the needle rod in place as described. In the alternate arrangement, the separable member can be formed without a severed wall or gap in the wail.

In preparation for filling the syringe, separable member 199 is separated from piston 198 in FIG. 23 by pushing down on the plunger with the needle rod and needle locked in position shown in FIG. 22. Separable member 199 is now easily and visibly seen in a separated position by locking at the syringe to serve as a warning or indicia that the syringe has been armed for use. Separable member 199 in cross section has a trapezoidal shape which prevents it from being reinserted into the hollow opening 201 of the piston by subsequent retraction on the plunger so that it cannot be reinserted into hollow opening 201 in the piston. It is flexibly resilient so that it can be separated from opening 201 in the piston seen in FIGS. 23 and 24.

After the air has been expelled from variable chamber 75, the plunger is partially withdrawn to fill the variable chamber with injection fluid in the usual manner. The separable member continues to be separated. When the plunger is then depressed to inject the fluid, the piston reaches the bottom of lower portion 192 and just as the last of the fluid is expelled in the variable chamber, release 220 on the plunger separates locking surfaces 208 or 211 to release the locking means and permit complete retraction of the needle assembly under the influence of biasing member 218 to produce the used position of FIG. 24. FIG. 24 shows the plunger completely depressed and the needle and needle rod retracted into the syringe body. The retracted position is permanent because the separable member can never be reconnected with the piston at the end of the plunger because of its shape. It will not fit back into the hollow space in the piston, and therefore no amount of action of the plunger will re-extend the needle. The syringe is permanently disarmed.

The embodiment of FIGS. 7-26 are especially suited for ease of assembly of the syringe components. In FIG. 18, for example, the plunger and needle assembly are frictionally engaged and installable as an installable unit into the syringe body. The installable unit preferably includes biasing member and stop member and the plunger guide plug fitted for installation into the plunger opening of the upper syringe body portion. In the best mode, it is believed preferable to preengage the separable member and the groove or other connection with the needle rod assembly before shipment if the additional length due to extension of the plunger as shown in FIG. 21 can be tolerated. This has the advantage of ease of assembly and eliminates the step of seating the separable member in the groove which the user would have to do before the needle could be locked in use position. It also means that the stop member 216 could be omitted since its main function is to restrain the needle assembly from moving up while the separable member is seated in preparation for locking the needle assembly. Also in the best mode, the guide members 222 can be omitted if sufficient guiding surface structure for the plunger arms is provided at plug member 197.

Figure 25:
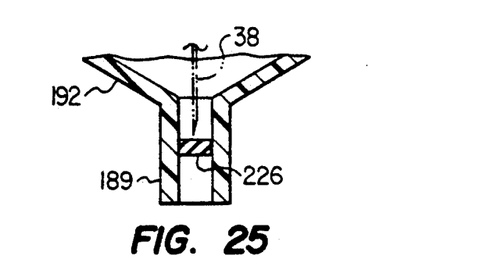
FIG. 25 shows a simple rubber seal in the tip of the syringe, the seal being penetrated by the needle to form a seal during the arming process.

In FIG. 25, a simple resilient seal plug member 226 may be installed in the opening of tip 189 either with or without the presence of seal 204 on the end of the needle rod. It can replace seal 204 and is especially useful as a seal for small syringes like the types used to inject insulin. The process of locking the needle rod causes the needle to puncture seal 226 as the needle is extended. The seal keeps any foreign material or contamination from entering the fluid chamber.

Figure 26:
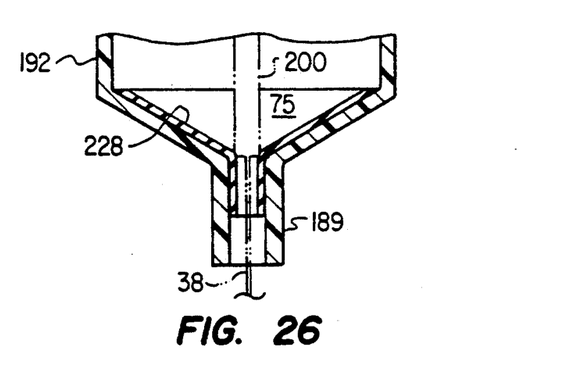
FIG. 26 shows a conical shaped seal lying in the bottom of the injection chamber and partway through the tip for sealing the end of the needle rod with the end of the needle rod shown schematically in dotted outline.

A resilient conical seal 228 is configured in the conical bottom end of body portion 192 and a tubular stem portion extends into the opening of tip 189. This makes it possible to eliminate seal 204 since the end of the needle rod seals against the conical seal simultaneously as the needle rod is being locked. Many other seal configurations and combinations can be used.

The advantages and improvements of the present invention are now clearly seen. By placing the retraction spring completely behind the piston assembly 20, a larger spring can be used without displacing the volume of fluid chamber 75. Only a small thin needle rod protrudes into the fluid chamber. The shape of the piston in FIGS. 18-24 could be like that of the other Figures to conform to a conical shape at the bottom of syringe body portion 192. The piston shown in the seventh embodiment of FIG. 18 permits the end of body portion 192 to be flat instead of conical in order to displace all the injection fluid when the plunger is fully depressed.

A safety indicator shows visibly whether the syringe has ever been used. Indicia are permanently uncovered or an arming bar permanently released to show if the syringe has ever been used. In the embodiments of FIGS. 7-26, the process of loading the syringe with fluid permanently and irreversibly disconnects the plungers from the needle rod. After disconnection and subsequent retraction, the needle cannot be re-extended by operation of the plunger.

An additional advantage with the present invention is that essentially all of the injection fluid is removed from fluid chamber 75 before the needle retraction mechanism is activated. Thus no fluid is lost through the tubular opening of the tip after the seal is broken and the needle 38 is retracted. At the same rime, the mechanism of the present invention prevents a user from cleaning and reusing the assembly, because the only way to clean the mechanism is to remove all of the fluid in the syringe, which would activate the retraction device. Once the needle has been retracted into the cylinder of the syringe, it cannot be accessed unless the cylinder itself is broken open. Thus, as long as there is no residue within the fluid chamber, one can be assured that the syringe has not been used.

An important advantage of the present invention is that the needle assembly is retracted automatically after all of the fluid has been forced out of the chamber. This automatic action prevents a medical worker or a patient from being inadvertently stuck by the needle after it has been withdrawn from the patient. It also prevents any further undesirable use of the hypodermic syringe by another user. Moreover, as the needle begins to retract at the point when the fluid injection has been completed, the fluid seal is broken and releases any vacuum formed between fluid chamber 75 and the patient, so that no bodily fluid is removed from the patient's body.

Some additional embodiments are included within the scope of this invention. The needle 38 and rod 40 may be combined as a single component. Also lock tabs 32 and 33 may be replaced by an annular lock ring, and dual cusps 80 and 81 may be replaced by an annular abutment. Other obvious variations may be made to the preferred embodiments shown without departing from the spirit of the invention or the scope of the claims.

What is claimed is:

1. A nonreusable retractable syringe for injecting fluid into a body, comprising:
   (a) a hollow syringe body having a lower end with a fluid cavity and tip and an upper end having an opening for a plunger;
   (b) a plunger extending through the opening having within the body a piston means movable in sliding sealed contact with the walls of the fluid cavity below a locking means to define a variable chamber for injection fluid;
   (c) a needle permanently attached to a movable needle assembly having a retracted position entirely within the body and an extended position wherein the needle is sealingly extended from the tip of the body for use;
   (d) locking means for releasably locking the needle assembly with the needle in the extended position, said locking means being positioned behind the piston means when the piston means is slidingly mounted in said variable chamber; and
   (e) retraction means disposed behind the piston means for causing the needle to be permanently withdrawn into the retracted position automatically in response to depression of the plunger to inject fluid.

2. The nonreusable syringe of claim 1 wherein the needle assembly is movable with the plunger before the needle assembly is locked into position.

3. The nonreusable syringe of claim 2 wherein a portion of the plunger acts on the needle assembly to operate the locking means.

4. The nonreusable syringe of claim 3 wherein the plunger moves independently in sliding sealed contact with the needle assembly after the needle assembly is locked.

5. The nonreusable syringe of claim 1 wherein the plunger and needle assembly are frictionally engaged and installable as an installable unit into the syringe body.

6. The nonreusable syringe of claim 5 wherein the installable unit includes a biasing member comprising part of the retraction means.

7. The nonreusable syringe of claim 6 wherein said biasing member is connected between the needle assembly and a plunger guide fitted for installation into the plunger opening as part of the installable unit.

8. The nonreusable syringe of claim 7 wherein the installable unit includes a stop member which positions the needle assembly in the retracted position to prevent the needle assembly from retracting beyond the retracted position.

9. The nonreusable syringe of claim 8 wherein the separable member is permanently separated from the plunger by movement of the plunger after the needle assembly is locked to serve as a permanent warning indicia which can show that the syringe has been used.

10. The nonreusable syringe of claim 9 wherein the separable member is removably held in a cavity in the piston until force is applied in excess of that necessary to operate the locking means, the separable member being shaped so that it cannot reenter the cavity.

11. The nonreusable syringe for injecting fluid into a body, comprising:
   (a) a hollow syringe body having a fluid cavity and tip at one end and an opening for a plunger;
   (b) a plunger extending through the opening having within the body a piston means in sliding sealed contact with the walls of the fluid cavity to define a variable chamber for injection fluid;
   (c) a needle connected to a movable needle assembly having a retracted position entirely within the body and an extended position wherein the needle is sealingly extended from the tip of the body for use, said needle assembly having an elongated needle rod from which said needle extends in fluid communication with a lower portion thereof so that said needle communicates with the variable chamber when the needle is in the extended position;
   (d) locking means for releasably locking the needle assembly with the needle in the extended position; and
   (e) retraction means for causing the needle to be permanently withdrawn into the retracted position automatically in response to depression of the plunger to inject fluid.

12. A nonreusable retractable syringe for injecting fluid into a body, comprising:
   (a) a hollow syringe body having a fluid cavity and tip at one end and an opening for a plunger;
   (b) a plunger extending through the opening having within the body a piston means in sliding sealed contact with the walls of the fluid cavity to define a variable chamber for injection fluid;
   (c) a needle connected to a movable needle assembly having a retracted position entirely within the body and an extended position wherein the needle is sealingly extended from the tip of the body for use, said needle assembly having an elongated needle rod from which said needle extends in fluid communication with a lower portion thereof so that said needle communicates with the variable chamber when the needle is in the extended position;
   (d) locking means for releasably locking the needle assembly with the needle in the extended position, wherein said locking means comprises one or more locking surfaces mounted on the needle rod and movable therewith to engage one or more cooperating locking surfaces on the syringe body, to releasably lock the needle assembly with the needle in the extended position; and
   (e) retraction means for causing the needle to be permanently withdrawn into the retracted position automatically in response to depression of the plunger to inject fluid.

13. The nonreusable syringe of claim 12 wherein the retraction means includes a portion of the plunger, which upon depression of the plunger to expel fluid from the variable chamber, comprises a release which separates said locking surfaces to release the locking means and permit retraction of the needle assembly under influence of a biasing retraction force.

14. The nonreusable syringe of claim 13 wherein said locking surfaces mounted on the needle rod and the release on the plunger are adapted for mutual relief so that part of the needle rod and said locking surfaces thereon may pass unimpeded through the release portion of the plunger when retraction occurs.

15. The nonreusable syringe of claim 12 wherein the retraction means comprises said cooperating surfaces being formed in the syringe body just below an enlarged portion of the syringe body and said locking surfaces are transverse extensions of said needle rod.

16. The nonreusable syringe of claim 15 wherein the enlarged portion of the syringe body includes at least a grooved portion for guiding the transverse extensions of the needle rod to said cooperating surfaces.

17. The reusable syringe of claim 16 wherein the retraction means includes a release on the plunger which releases the locking surfaces upon full depression of the plunger after the needle assembly is locked into the extended position.

18. The reusable syringe of claim 17 wherein the transverse extension on the needle rod and the plunger release are adapted for mutual relief so that the transverse extensions may pass unimpeded through the release portion of the plunger during retraction.

19. The nonreusable retractable syringe for injecting fluid into a body, comprising:
   (a) a hollow syringe body having a lower end with a fluid cavity and tip and an upper end having an opening for a plunger;
   (b) a plunger extending through the opening having within the body a piston means movable in sliding sealed contact with the walls of the fluid cavity below a locking and retraction means to define a variable chamber for injection fluid;
   (c) a needle connected to a movable needle assembly having a retracted position entirely within the body and an extended position wherein the needle is sealingly extended from the tip of the body for use;
   (d) locking means for releasably locking the needle assembly with the needle in the extended position; and
   (e) retraction means disposed behind the piston means for causing the needle to be permanently withdrawn into the retracted position automatically in response to depression of the plunger to inject fluid.

20. A nonreusable retractable syringe for injecting fluid into a body, comprising:
   (a) a hollow syringe body having a lower end with a fluid cavity and tip and an upper end having an opening for a plunger;
   (b) a plunger extending through the opening having within the body a piston means movable in sliding sealed contact with the walls of the fluid cavity below a locking means to define a variable chamber for injection fluid;
   (c) a needle connected to a movable needle assembly having a retracted position entirely within the body and an extended position wherein the needle is sealingly extended from the tip of the body for use, the needle assembly being movable with the plunger before the needle assembly is locked into position;
   (d) locking means for releasably locking the needle assembly with the needle in the extended position;
   (e) the plunger including a separable member in sliding contact with the needle assembly and engageable therewith to operate the locking means, the plunger moving independently in sliding sealed contact with the needle assembly after the needle assembly is locked; and
   (f) retraction means disposed behind the piston means for casing the needle to be permanently withdrawn into the retracted position automatically in response to depression of the plunger to inject fluid.

* * * * *

UNITED STATES PATENT AND TRADEMARK OFFICE
CERTIFICATE OF CORRECTION

PATENT NO. : 5,267,961
DATED : December 7, 1993
INVENTOR(S) : Thomas J. Shaw

It is certified that error appears in the above-indentified patent and that said Letters Patent is hereby corrected as shown below:

Column 15, line 64, delete "8" and substitute --20--.

Column 16, line 6, delete "The" and substitute --A--.

Column 16, line 6, add --retractable-- between "nonreusable" and "syringe."

Column 16, line 11, delete "with" and substitute --within--.

Column 17, line 26, delete "The" and substitute --A--.

Column 18, line 37, delete "casing" and substitute --causing--.

Signed and Sealed this

Third Day of May, 1994

Attest:

BRUCE LEHMAN

*Attesting Officer*　　　　Commissioner of Patents and Trademarks